(12) United States Patent
Miller et al.

(10) Patent No.: US 10,548,790 B2
(45) Date of Patent: Feb. 4, 2020

(54) POST-SURGICAL SUPPORT MEMBER FOR SURGICAL SITE

(71) Applicants: Andrew Miller, Philadelphia, PA (US); Alexander R. Vaccaro, Gladwyne, PA (US)

(72) Inventors: Andrew Miller, Philadelphia, PA (US); Alexander R. Vaccaro, Gladwyne, PA (US)

(*) Notice: Subject to any disclaimer, the term of this patent is extended or adjusted under 35 U.S.C. 154(b) by 843 days.

(21) Appl. No.: 15/140,867

(22) Filed: Apr. 28, 2016

(65) Prior Publication Data

US 2016/0317722 A1 Nov. 3, 2016

Related U.S. Application Data

(60) Provisional application No. 62/153,596, filed on Apr. 28, 2015.

(51) Int. Cl.
| | | |
|---|---|---|
| *A61G 7/057* | (2006.01) | |
| *A61G 7/07* | (2006.01) | |
| *A61G 13/12* | (2006.01) | |
| *A61M 1/00* | (2006.01) | |

(52) U.S. Cl.
CPC ............ *A61G 7/07* (2013.01); *A61G 7/05723* (2013.01); *A61G 13/1225* (2013.01); *A61M 1/0088* (2013.01)

(58) Field of Classification Search
CPC .............. A61G 13/122; A61G 13/1225; A61G 13/123; A61G 13/128; A61G 7/05723; A61G 7/07

USPC ...................................................... 5/630–651
See application file for complete search history.

(56) References Cited

U.S. PATENT DOCUMENTS

| | | | | |
|---|---|---|---|---|
| 1,595,698 A | * | 8/1926 | Wilson ................. | A47C 20/027 5/630 |
| 2,056,767 A | * | 10/1936 | Blath .................. | A61G 7/05723 128/889 |
| 2,085,296 A | * | 6/1937 | Gerturde ............ | A61G 7/05723 128/889 |
| 3,063,448 A | * | 11/1962 | Scholl ................ | A61F 13/063 128/894 |
| 3,606,886 A | * | 9/1971 | Bittner ............... | B29C 67/20 128/894 |
| 3,757,366 A | * | 9/1973 | Sacher ................ | A47C 21/044 297/180.13 |
| 3,811,140 A | | 5/1974 | Burpo | |
| 4,206,524 A | * | 6/1980 | Cook .................. | A61G 7/057 5/630 |
| 4,468,824 A | * | 9/1984 | O'Hanlan ........... | A47C 27/085 5/630 |
| 4,752,064 A | * | 6/1988 | Voss .................... | A61G 13/12 5/622 |
| 4,779,297 A | * | 10/1988 | Sturges .............. | A47C 20/026 5/630 |
| 4,840,362 A | | 6/1989 | Bremer et al. | |
| 5,014,375 A | | 5/1991 | Coonrad et al. | |
| 5,364,339 A | * | 11/1994 | Carver ............... | A61F 13/0259 128/888 |

(Continued)

*Primary Examiner* — Susan S Su
(74) *Attorney, Agent, or Firm* — BakerHostetler

(57) ABSTRACT

A post-surgical support member is configured to be placed post-surgically between a supine patient and a support surface so as to isolate an anatomical load from a post-surgical wound against the support surface, the anatomical load produced by the weight of the supine patient.

21 Claims, 8 Drawing Sheets

(56) References Cited

U.S. PATENT DOCUMENTS

| | | | |
|---|---|---|---|
| 5,708,998 A * | 1/1998 | Torbik | A47G 9/10 5/636 |
| 6,557,197 B1 | 5/2003 | Graham | |
| 6,920,881 B2 | 7/2005 | Narula et al. | |
| 6,966,088 B1 | 11/2005 | Hu | |
| 7,141,032 B2 * | 11/2006 | Flam | A61F 13/069 602/61 |
| 7,534,927 B2 | 5/2009 | Lockwood et al. | |
| 8,361,043 B2 | 1/2013 | Hu et al. | |
| 2001/0043943 A1 * | 11/2001 | Coffey | A61F 13/02 424/447 |
| 2006/0084902 A1 | 4/2006 | Schleicher et al. | |
| 2006/0265808 A1 * | 11/2006 | Phillips | A47G 9/10 5/637 |
| 2007/0056108 A1 * | 3/2007 | Nikolopoulos | A61H 37/00 5/644 |
| 2008/0010751 A1 * | 1/2008 | Kemper | A47C 27/146 5/655.9 |
| 2012/0079659 A1 * | 4/2012 | Loos | A47G 9/10 5/636 |
| 2013/0255699 A1 * | 10/2013 | Squitieri | A61F 5/34 128/892 |
| 2014/0155848 A1 | 6/2014 | Antalek | |
| 2014/0359943 A1 * | 12/2014 | Casta-Baez | A47G 9/109 5/636 |

* cited by examiner

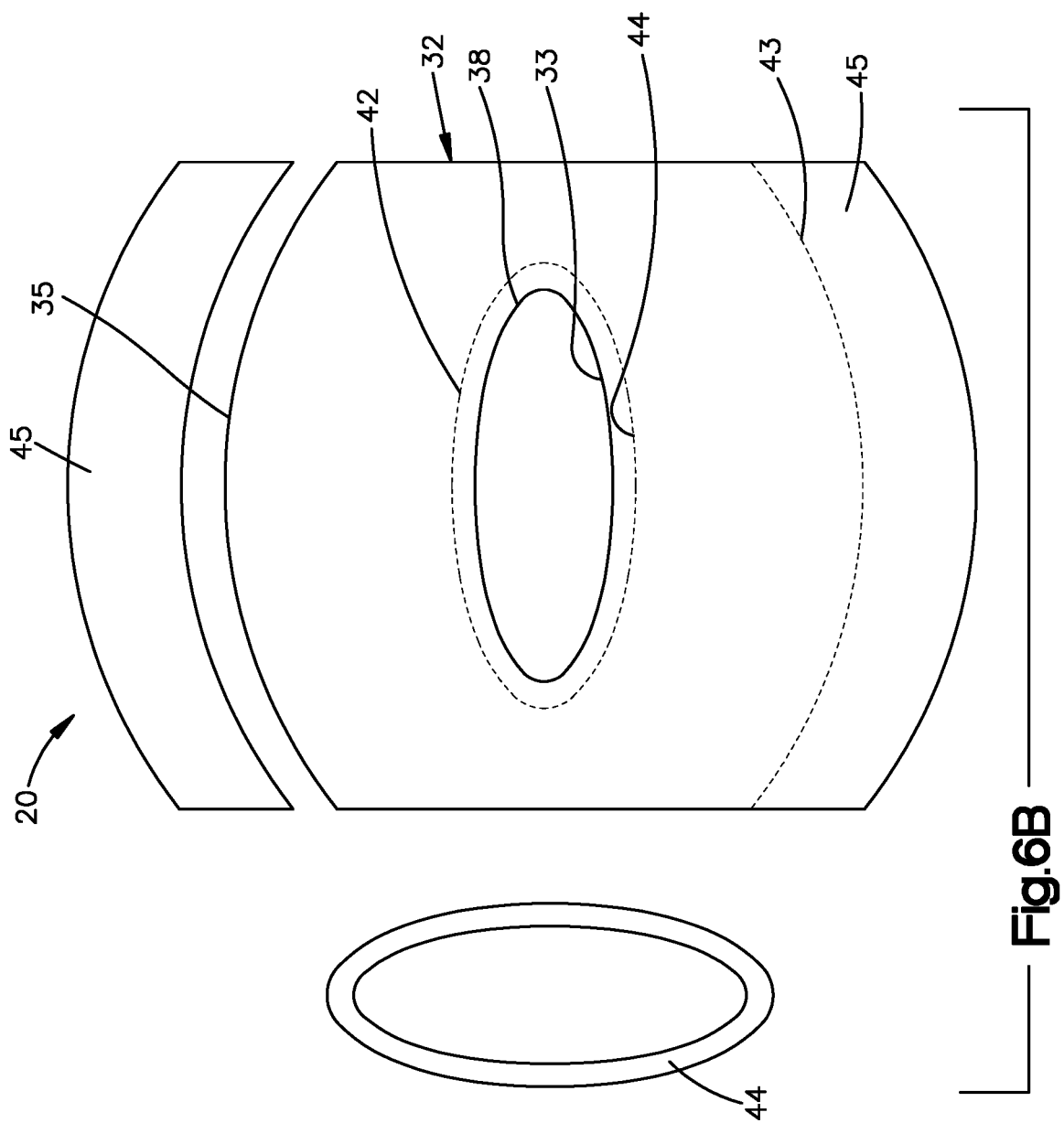

POST-SURGICAL SUPPORT MEMBER FOR SURGICAL SITE

CROSS-REFERENCE TO RELATED APPLICATIONS

This claims the benefit of U.S. Patent Application Ser. No. 62/153,596 filed Apr. 28, 2015, the disclosure of which is incorporated by reference as if set forth in its entirety herein.

BACKGROUND

Conventional spinal surgical procedures involve creating an incision in an epidermis of the patient, creating a conduit to a target location, performing at least one surgical operation at the surgical location, removing the surgical implements, and closing the surgical incision. After completion of the surgery, the patient typically lays in a supine position against a support surface, which can be defined by a bed or cot or the like, thereby causing the closed incision to bear against the support surface under an anatomical load that is produced under the weight of the patient.

SUMMARY

The following Summary is provided to introduce a selection of concepts in a simplified form that are further described below in the Detailed Description. This Summary is not intended to identify key features or essential features of the invention, nor is it intended to be used to limit the scope of the invention. Reference is made to the claims for that purpose.

In one embodiment, a post-surgical support member configured to support a patient that is supine on a support surface following a surgical procedure that has created a surgical wound. The support member can include a compressible body having a first surface configured to face the supine patient, and a second surface opposite the first surface along a transverse direction and configured to face the support surface. The support member defines an aperture that extends at least into the body from the first surface toward the second surface. The support member is configured to be placed against the patient such that the surgical wound is aligned with the aperture along the transverse direction so as to isolate an anatomical load between the surgical wound and the support surface along the transverse direction, the anatomical load produced by the weight of the supine patient.

BRIEF DESCRIPTION OF THE SEVERAL VIEWS OF THE DRAWINGS

The foregoing summary, as well as the following detailed description, is better understood when read in conjunction with the appended drawings. There is shown in the drawings example embodiments, in which like reference numerals correspond to like reference numerals throughout. The present invention is not intended to be limited to the specific embodiments and methods disclosed, and reference is made to the claims for that purpose.

FIG. 6B is a top plan view of the support member as illustrated in FIG. 6A, after removal of perforated regions at perforations illustrated in FIG. 6A;

DETAILED DESCRIPTION

Figure 1:
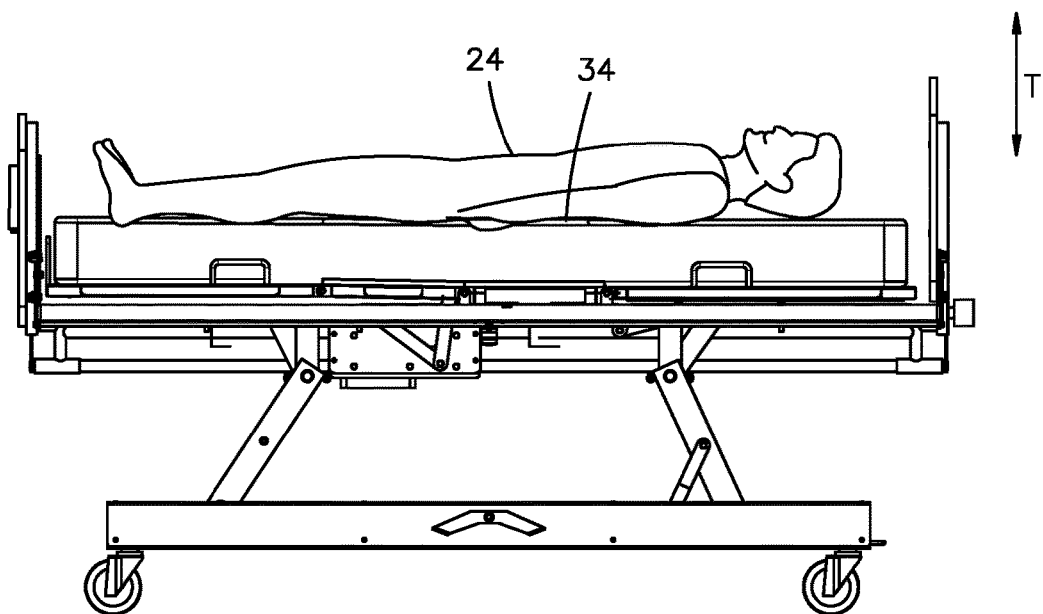
FIG. 1 is a schematic illustration of a supine patient supported by a support surface following a surgical procedure.
Figures 2A, 2B:
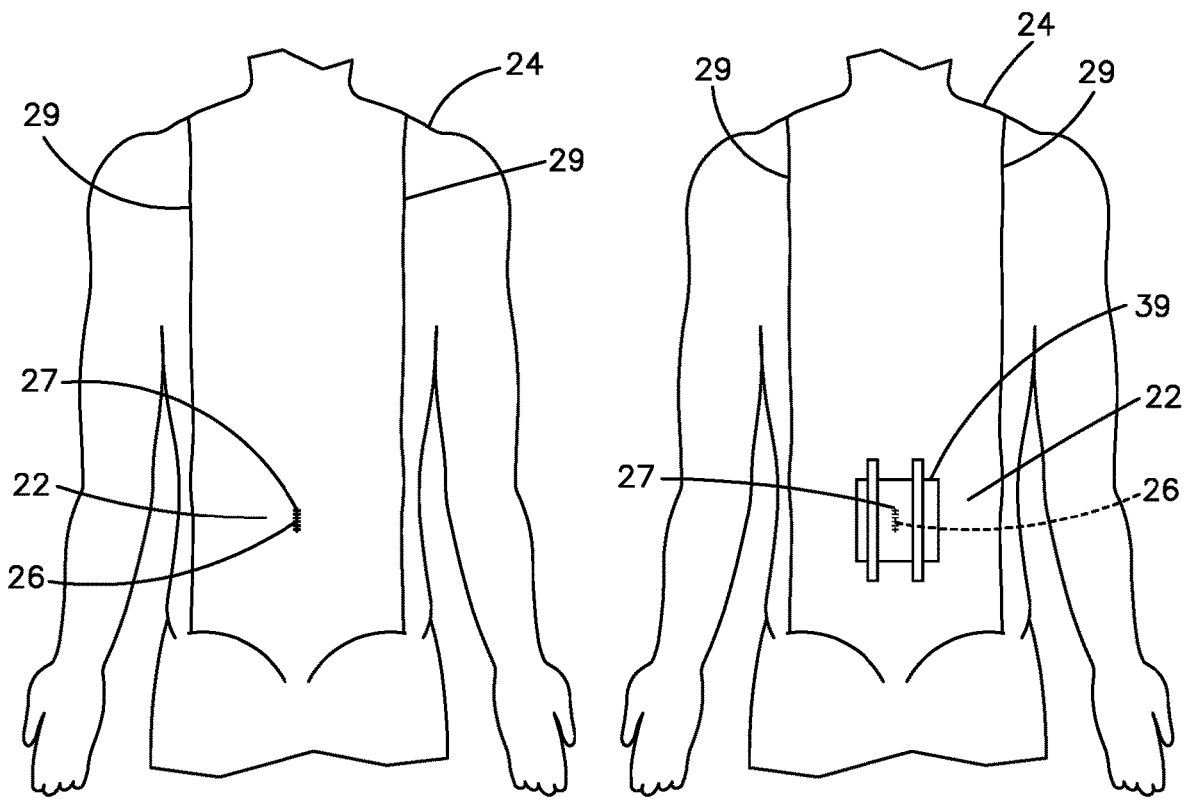
FIG. 2A is an elevation view of a posterior aspect of the patient illustrated in FIG. 1, showing a surgical wound.
FIG. 2B is an elevation view of the posterior aspect of the patient illustrated in FIG. 2A, showing a post-surgical dressing that covers the surgical wound.
Figure 3:
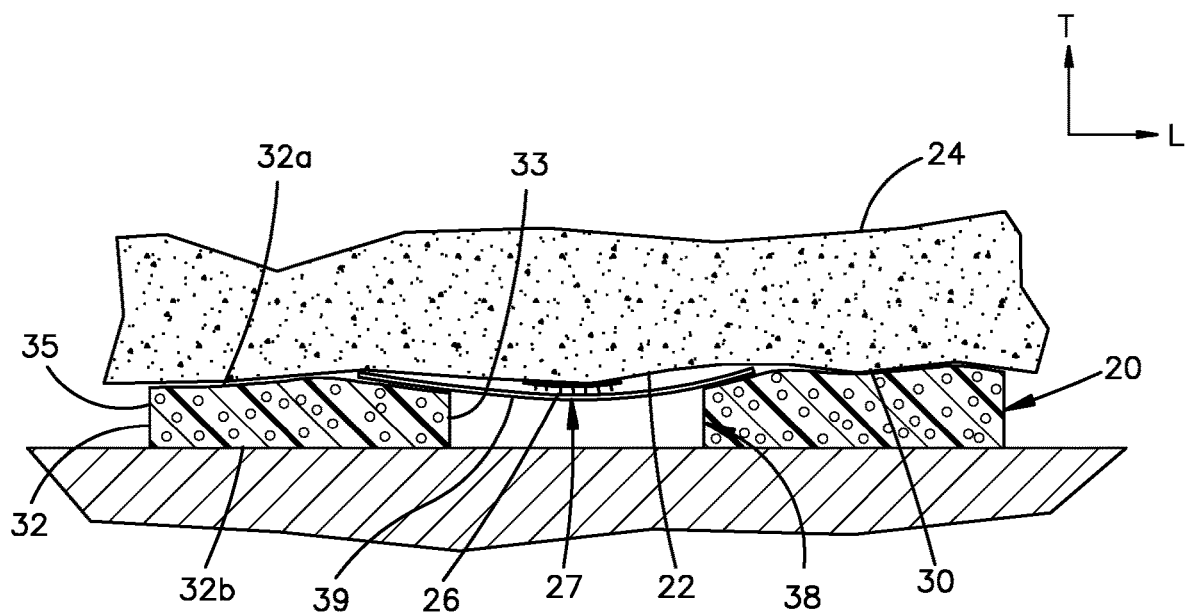
FIG. 3 is an enlarged region of the patient illustrated in FIG. 1 shown supported by a support member constructed in accordance with one embodiment, shown in cross-section.

Referring to FIGS. 1-3, a post-surgical support member 20 is configured to support a supine patient 24 following a surgical procedure that has produced a surgical wound 26 at a surgical site 27, thereby promoting wound healing. The surgical wound 26 can, for instance, be created by a surgical incision that has been post-operatively closed. For instance, the surgical incision can be sutured and/or covered with an adhesive closure strip, such as a Steri-Strip™ closure, commercially available from 3M Corporation, having a principal place of business in St. Paul, Minn.). Alternatively or additionally, the surgical wound 36 can be at least partially closed with a wound drainage system such as a Jackson-Pratt drain, or at least partially closed with a wound vacuum assisted closure (wound VAC).

In one common application, the patient 24 has undergone a spinal surgical procedure, such that the surgical wound 26 is located at the spinal region of the supine patient 24. Thus, in one example, the surgical incision can extend through an epidermis 22 of the supine patient 24, and through the soft tissue below the epidermis 24 toward the spinal column. For instance, the spinal surgical procedure can be a spinal decompression, a spinal fusion, or other suitable spinal surgical operation, though it is appreciated that the surgical procedure is not intended to be limited to spinal surgical procedures unless otherwise indicated. It is recognized that a post-surgical dressing 39 typically covers the surgical wound 26. Thus, the surgical site 27 can be defined by the surgical wound 26 individually, or in combination with at least a portion of a post-surgical dressing 39 that is aligned with the surgical wound 26 in the anterior-posterior direction.

It should be appreciated that the surgical wound 26 is disposed at a weight-bearing location of the patient 24 when the patient 24 is supine on a support surface 34. The support surface 34 can be defined by a bed, cot, couch, or other resting surface that supports the supine patient 24 following the surgical procedure as the surgical wound 26 heals. The present inventors have recognized that when the supine patient 24 rests on the support surface 34 in the conventional manner, a portion of the patient's weight bears directly against the surgical site 27 along the anterior-posterior direction. That is, the surgical site 27 is directly supported by the support surface 34. As described above, the weight of the patient 24 can create a substantially constant anatomical load against the surgical site 27, which can adversely affect the ability of the surgical wound 26 to heal, even when dressed. Accordingly, as will now be described, the support member 20 is configured to support the epidermis 22 at a support location 30 that is spaced outboard from the surgical site 27 so as to at least partially isolate the anatomical loads produced by the weight of the supine patient 24 from the surgical wound 26. With respect to the medial lateral direction, the support location 30 can be included at a location between the surgical wound 26 and the anatomical posterior axillary lines 29 of the patient 24. In one example, the support location 30 can be contained between the surgical wound 26 and the anatomical posterior axillary lines 29 of the patient 24 with respect to the medial-lateral direction. With respect to the cranial-caudal direction, the support location 30 can extend any suitable distance as desired from the surgical wound 26, depending on the nature and dimensions of the surgical wound 26. In one example, the distance can be the distance that the surgical wound 26 is spaced from the posterior axillary lines 29 along the medial lateral direction.

The post-surgical dressing 39 can be localized at the surgical wound 26. Additionally, the post-surgical dressing 39 can be spaced from the surgical wound 26 in one or both of the medial lateral direction and the cranial-caudal direction. Accordingly, the support location 30 can be defined by the epidermis 22 alone, or the epidermis 22 in combination with a portion of the post-surgical dressing 39. Thus, at least a portion of the support member 20 up to an entirety of the support member 20 can overlap the epidermis 22, alone, for instance at a location outboard of the post-surgical dressing 39. Alternatively, at least a portion of the support member 20 up to an entirety of the support member 20 can overlap both the epidermis 22 and the post-surgical dressing 39 with respect to the anterior-posterior direction. It is recognized that the post-surgical dressing 39 may be changed and replaced with another post-surgical dressing 39 at various intervals throughout the surgical wound healing process.

The support member 20 can have a thickness that is suitable to maintain the surgical site 27 at a location spaced above the support surface 34 along a transverse direction T. The transverse direction T can be coincident with the anterior-posterior direction during operation of the support member 20. As a result, the support member 20 is configured to isolate the anatomical load produced by the weight of the patient 24 between the surgical site 27 and the support surface 34 along the anterior-posterior direction. Thus, the anatomical load does not travel directly from the surgical site 27 to the support surface 34 along the anterior-posterior direction. It will thus be appreciated that the anatomical load does not travel from the surgical wound 26 to the support surface 27, either directly or through the post-surgical dressing 39, along the anterior-posterior direction. Rather, the anatomical load is diffused through the support member 20.

In one example, the support member 20 can be configured to at least substantially surround or entirely surround the surgical site 27. The support member 20 is thus configured to be disposed between the support location 30 and the support surface 34 when the patient 24 is supine on the support surface 34 following the surgical procedure. Thus, an anterior-posterior load produced by the weight of the supine patient 24 that would otherwise bear directly on the surgical wound 26 instead bears against the support member 20 at the support location 30.

Figure 4:
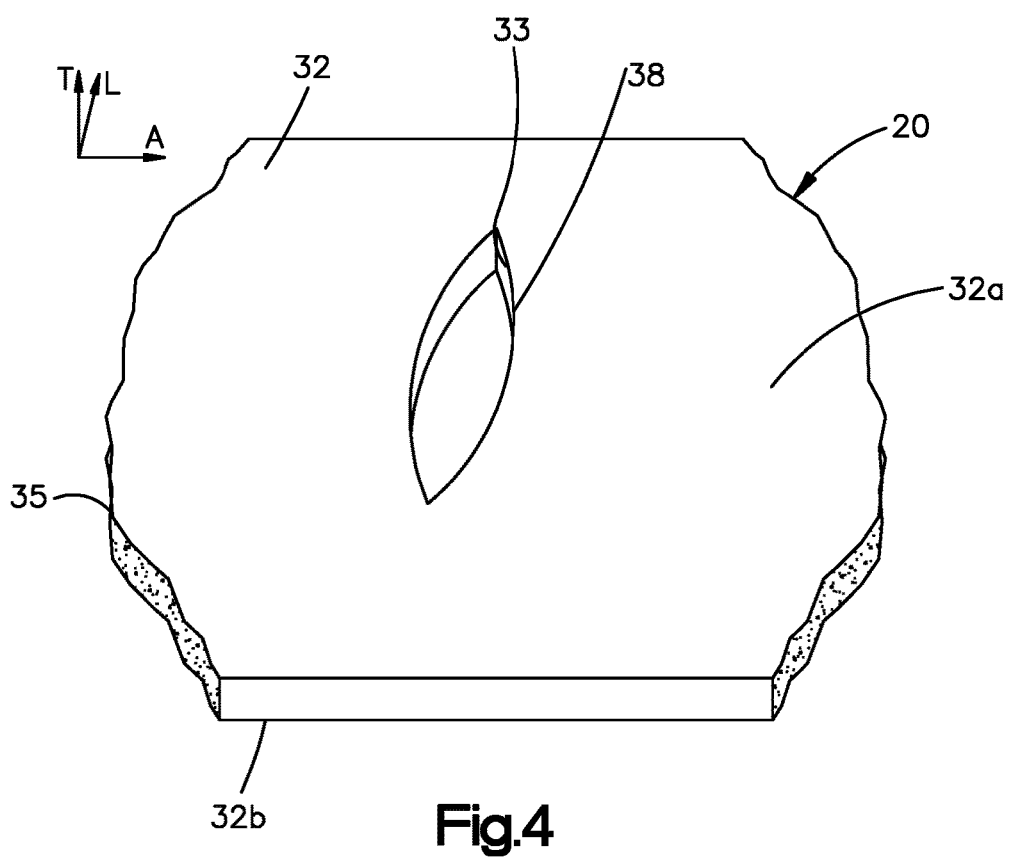
FIG. 4 is a perspective view of the support member illustrated in FIG. 3.

Referring now to also FIG. 4, the support member 20 includes a body 32 that defines a first surface 32a and a second surface 32b opposite the first surface 32a along the transverse direction T. The body 32 can further define an outer perimeter 35 that extends from the first surface 32a to the second surface 32b. As described below, the support member 20 can be compressible along the transverse direction T from a relaxed state to a compressed state. Thus support member 20 can define a relaxed thickness in the transverse direction T when the support member 20 is in the relaxed state, and a compressed thickness in the transverse direction T when the support member 20 is in the compressed state, wherein the compressed thickness is less than the relaxed thickness. The compressed thickness and the relaxed thickness are measured from the first surface 32a to the second surface 32b along the transverse direction T. The compressed thickness and the relaxed thickness can be as desired. For instance, in one example, the relaxed thickness of the support member 20 can be between and including approximately one-half inch and approximately 6 inches, such as between and including approximately one-half inch and approximately 3.5 inches, such as between and including approximately one-half of an inch and approximately 2 inches, such as between and including approximately three-quarters of an inch and approximately 1 inch. It is recognized that longer surgical wounds 26 can benefit from increased relaxed thicknesses.

The first surface 32a can be substantially planar along a longitudinal direction L and a lateral direction A, wherein the longitudinal direction L and the lateral direction A are perpendicular to both each other and perpendicular to the transverse direction T. Similarly, the second surface 32b can be substantially planar along the longitudinal direction L and the lateral direction A. Thus, the first and second surfaces 32a and 32b can be oriented substantially parallel to each other. It should be appreciated, of course, that the first and second surfaces can have any orientation as desired such that the support member 20 is configured to isolate the anatomical loads between the surgical site 27 and the support surface 34 along the anterior-posterior direction.

The first surface 32a is configured to face the epidermis 22 of the supine patient 24 during operation. In particular, the first surface 32a is configured to face the support location 30 that is disposed outboard from the surgical wound 26. At least a portion up to an entirety of the support location 30 can be defined by the epidermis 22. Alternatively or additionally, at least a portion up to an entirety of the support location 30 can be defined by the post-surgical dressing 39. Thus, the first surface 32a is configured to provide physical support to the support location 30 when the body 32 is disposed between the support surface 34 and the supine patient 24. Accordingly, the first surface 32a receives weight of the patent from the support location 30. In one embodiment, the first surface 32a can be configured to adhesively attach to the support location 30. It may be preferable in certain circumstances that the first surface 32a attaches to the epidermis 22 at the support location 30 so as to facilitate easy removal of the support member 20 without compromising the integrity of the post-surgical dressing 39. Because the weight of the patient 24 can travel from the support location 30 through the support member 20 along the transverse direction T, the support member 20 can be said to directly support the support location 30. The first surface 32a can be beveled or otherwise tapered at the outer perimeter so as to provide a gradual decrease in thickness at the outer perimeter 35 for patient comfort.

The second surface 32b is configured to face the support surface 34. Thus, it should be appreciated that the first and second surfaces 32a and 32b are configured to be disposed between the epidermis 22 and the support surface 34. Thus, the weight of the patient that is transferred from the support location 30 to the first surface 32a is further transferred through the support member 20, and delivered to the support surface 34 from the second surface 32b. It is recognized that an intermediate structure can be disposed between the second surface 32b and the support surface 34. In one example, the second surface 32b is configured to abut the support surface 34. Because the support member 20 spaces the surgical wound 26 from the support surface 34, the support member 20 can be referred to as a spacer. Similarly, the body 32 of the support member 20 can be referred to as a spacer body. As will now be described, when the support member 20 is disposed between the support surface 34 and the supine patient 24, the support member 20 receives anatomical loads produced from the weight of the supine patient 24, thereby isolating the anatomical loads along the anterior-posterior direction from the surgical site 27, and in particular from the surgical wound 26.

For instance, referring to FIG. 4, the body 32 of the support member can define an aperture 38 that extends along the transverse direction T at least into the first surface 32a. Thus, the body 32 can define an interior surface 33 that defines the perimeter of the aperture 38 with respect to a plane that is defined by the longitudinal direction L and the lateral direction A. Thus, the body 32 can extend from the interior surface 33 to the outer perimeter 35. The aperture 38, and thus the interior surface 33, can extend from the first surface 32a along a direction toward the second surface 32b. In one example, the aperture 38 can extend entirely through the body 32 from the first surface 32a to the second surface 32b. When the support member 20 supports the support location 30 of the surgical site 27, at least a portion of the aperture 38 can be aligned with the surgical site 27, and in particular with the surgical wound 26, along the transverse direction T. For instance, an entirety of the surgical wound 26 can be aligned with the aperture 38. Because the body 32 is disposed between the support location 30 of the surgical site 27 and the support surface 34, and the surgical wound 26 is aligned with the support surface 34 and the aperture 38 along the transverse direction T, the body 32 can maintain the surgical wound 26 at a location spaced from the support surface 34 along the transverse direction. Thus, the support member 20 can isolate the anatomical loads produced by the weight of the supine patient 24 along the anterior-posterior direction from the surgical wound 26.

In another example, the aperture 38 can extend from the first surface 32a toward the second surface 32b along the transverse direction T, but terminates at a base that is disposed between the first surface 32a and the second surface 32b with respect to the transverse direction T. The base can be spaced from the first surface 32a a sufficient distance along the transverse direction T such that the surgical wound 26 is spaced above the base when the support member 20 supports the supine patient 24 at the support location 30. Thus, the support member 20 can isolate the entirety of the anatomical load produced from weight of the supine patient 24 along the anterior-posterior direction from the surgical wound 26 as described above.

Alternatively, the base can be spaced from the surgical site 27 before the weight of the patient 24 bears against the support member 20, but can contact the surgical site 27 when the support location 30 of the supine patient 24 is supported by the support member 20. In this example, the support member 20 isolates a portion of the anatomical loads produced by the weight of the supine patient along the anterior-posterior direction from the surgical wound 26. It can thus be said that the support member 20 can isolate at least a portion of the weight of the anatomical loads produced from the weight of the supine patient 24 along the anterior-posterior direction from the surgical wound 26 when the patient 24 is supine and the support member 20 is disposed between the support location 30 and the support surface 34.

In one example, the body 32 of the support member 20 can have a hardness less than the hardness of the support surface 34. For instance, the body 32 of the support member 20 can be compressible so as to provide comfort to the supine patient 24 as the body 32 is compressed along the transverse direction T by the anatomical loads. Accordingly, the support member 20 can be compressed so as to define a thickness along the transverse direction T from the first surface 32a to the second surface 32b in the compressed state that is less than the thickness when the support member 20 is in the relaxed state.

Further, the body 32 of the support member 20 can be porous with respect to airflow through the body along a direction that is perpendicular to the transverse direction T, such that the support member 20 can allow ambient air to access the surgical site 27. In one example, the body 32 of the support member 20 can be made from a hypoallergenic or non-allergenic material. In one example, the body 32 can be made from a foam material. In a further example, the body 32 of the support member 20 can be a memory foam. For instance, the body 32 can be a polyurethane-based memory foam. In one example, the memory foam is medical grade. Further, the body 32 can be a viscoelastic polyurethane, or any suitable alternatively constructed memory foam. As one example, the polyurethane-based memory foam can be a Capu-Cell® Polyurethane Foam, commercially available from TMP Technologies, Inc., having a place of business at 1200. Northland Avenue, Buffalo, N.Y. 14215. Alternatively, the body 32 can be a silicone-based memory foam or any suitable alternative material.

In one example, because the body 32 is compressible, the body, and in particular the first surface 32a, can mold to the support location 30, including the epidermis, of the supine patient 24. The body 32 of the support member 20 can have any suitable porosity as desired. The porosity can be defined as a density that is measured in terms of pounds per cubic foot. It should be appreciated that the porosity of the body 32 can allow for breathability at the surgical site 27 without compromising the durability of the body 32 when the body 32 is compressed by the anatomical loads. In one example, the body 32 can have a density in a range that has a lower end and an upper end. The lower end of the range can be approximately 0.5 pounds per cubic foot, or alternatively approximately 2 pounds per cubic foot, and the upper end of the range can be approximately 10 pounds per cubic foot, or alternatively approximately 8 pounds per cubic foot. For instance, the range can include a lower range that is between and includes approximately 1.5 pounds per cubic foot and approximately 3 pounds per cubic foot. The range can include a middle range that is between and includes approximately 3 pounds per cubic foot and approximately 6 pounds per cubic foot. The range can further include an upper range that is between and includes approximately 6 pounds per cubic foot and approximately 10 pounds per cubic foot. It should be appreciated that the density is provided by way of example, only, and that the body 32 can have any suitable density as desired without departing from the present disclosure.

Figure 5A:
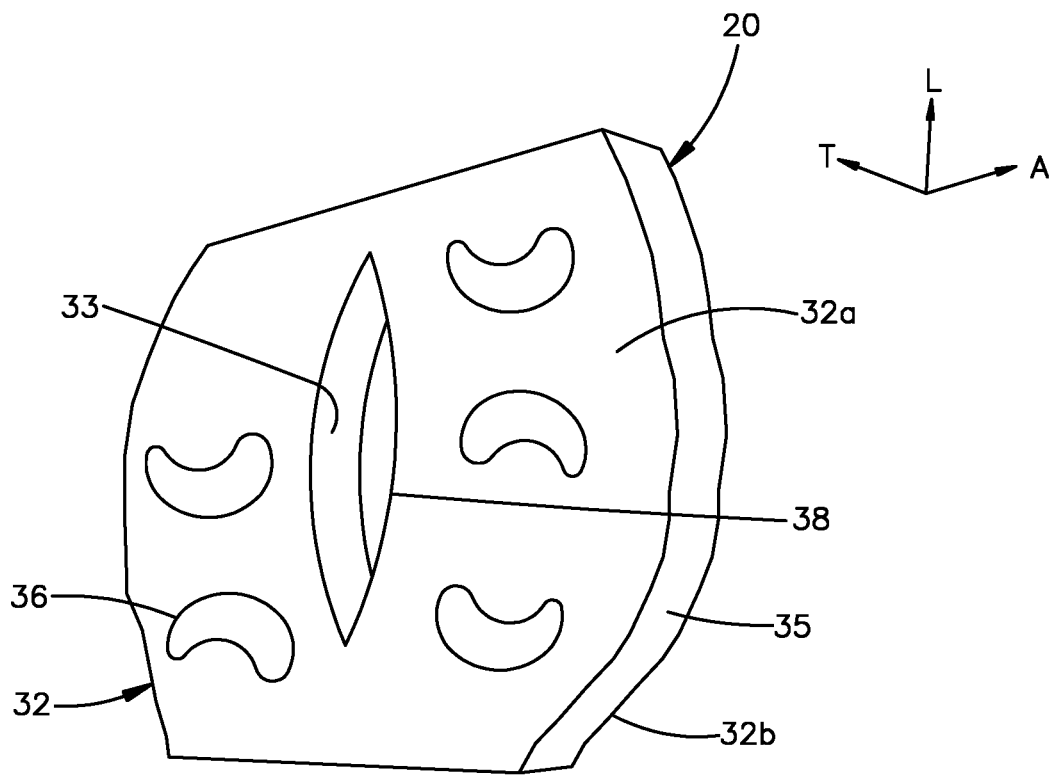
FIG. 5A is another perspective view of the support member illustrated in FIG. 4, showing a plurality of attachment members configured to attach to the patient.
Figure 5B:
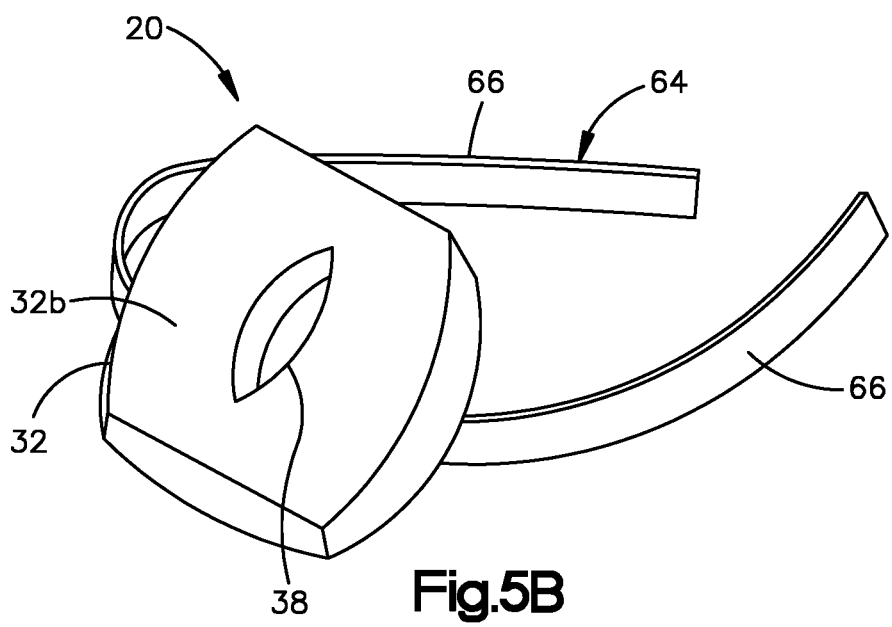
FIG. 5B is another perspective view of the support member illustrated in FIG. 4, showing including a harness.

Referring now also to FIGS. 5A-5B, the first surface 32a can be configured to abut the support location 30. For instance, as described above and shown in FIG. 5A, the support member 20 can be configured to attach to the support location 30 at the first surface 32a. For example, the support member 20 can include at least one attachment member 36 that is configured to attach the body 32 to the patient 24, such that the body is configured to support the support location 30 in the manner described above. In one example, the first surface 32a can carry at least one attachment member 36, such as a plurality of attachment members 36, configured to attach to the support location 30. Thus, at least a portion of the first surface 32a can attach to the epidermis 22 at a location spaced from the surgical wound 26 at a location between the axillary lines 29. In one example, the attachment member is configured to attach directly to the epidermis 22 at the support location 30. Alternatively or additionally, the first surface 32a can attach to the post-surgical dressing 39 at the support location 30, or to any suitable alternative structure that, in turn supports or is otherwise attached to the support location 30.

In one example, the attachment member 36 is configured as an adhesive that is carried by the first surface 32a and is suitable to adhesively attach to the support location 30. The adhesive can be configured as a glue, a tape, or any suitable alternative adhesive. The adhesive can be a double-sided adhesive so as to attach to both the first surface 32a and the support location 30. For instance, one side of the adhesive can attach to the first surface 32a, and the other side of the adhesive can be covered by a removable backing. The removable backing can be removed so as to expose the other side of the adhesive, which can then be applied to the support location 30.

The adhesive can be configured to attach to the epidermis 22 or the post-surgical dressing 39. Alternatively or additionally, one or both of the epidermis 22 and the post-surgical dressing 39 can similarly carry an adhesive that is configured to adhesively attach to the adhesive carried by the first surface 32a. It can be desirable for the attachment member 36 to be non-allergenic or hypo-allergenic, and skin friendly such that the attachment member 36 can be applied over the post-operative dressing 39 or the epidermis 22.

While the attachment member 36 can be configured as an adhesive in one embodiment, it should be appreciated that first surface 32 can attach to the support location 30 in accordance with any suitable alternative embodiment as desired. For instance, the attachment member 36 can be configured as a plurality of one of hooks and loops. The support location 30 can be attached to an attachment member that includes a plurality of the other of hooks and loops. The hooks and loops can interlock with each other so as to attach the body 32 of the support member 20 to the support location 30.

It is appreciated that it may be desirable to change the post-surgical dressing 39 from time to time. Accordingly, the body 32 can be removable from the support location 39 so as to enable easy access to the surgical site 27. Once the post-surgical dressing has been removed and replaced, the body 32 can be re-attached to the support location 30. For instance, the attachment member 36 can be re-attached to the support site 30. Alternatively, another attachment member 36 can be applied to the support member 20 so as to facilitate attachment to the surgical site in the manner described above. Thus, it should be appreciated that the support member 20 is configured to removably attach, and reattach, to the support location 30 as desired.

Referring to FIG. 5B, the support member can include a harness 64 that supports the body 32, and is configured to wrap around the patient's body so as to support the support member 20 at the support location 30 in the manner described herein. The harness 64 can include a pair of straps 66 that extend out from the body 32 and are configured to attach to each other so as to wrap around the patient's body, for instance at the abdomen. The straps 66 can support a buckle that latches so as to attach the straps to each other, or can define respective hooks and loops that attach to each other so as to attach the straps to each other, or can include any suitable apparatus that attaches the straps to each other, thereby securing the support member 20 to the patient 24 while the body 32 is aligned with the support location 30 as described above. Further, the straps 66 can be detached from each other when it is desired to remove the support member, for instance when changing the dressing 39. It should be appreciated that the support member 20 can include both the harness 64 and the at least one attachment member 36 as described above with reference to FIG. 5A.

The harness 64, the at least one attachment member 36, or both, are configured to attach the support member 20 to the support site 30 or otherwise support the support site 30 such that the surgical site 27 is aligned with the aperture 38 along the transverse direction T. Thus, the interior surface 33 can substantially circumscribe the surgical site 27. The support member 20 can be dimensioned in the medial-lateral direction such that an entirety of the support member 20 is disposed between the anatomical posterior axillary lines 29. That is, the outer perimeter 35 is disposed between the posterior axillary lines 29. The support member 20 can be dimensioned in the cranial-caudal direction any distance as desired, depending on the nature and dimensions of the surgical wound 26.

Referring again to FIG. 4, the aperture 38 can define any suitable dimensions as desired. For instance, the aperture 38 can define a length along a longitudinal direction L that is perpendicular to the transverse direction T. The aperture 38 can define a width along a lateral direction A that is perpendicular to both the longitudinal direction L and the transverse direction T. The length along the longitudinal direction L can be greater than the width along the lateral direction A. The length can be oriented in the same direction as the elongation of the surgical wound 26. Thus, depending on the shape and orientation of the surgical wound 26, the longitudinal direction L can define the cranial-caudal direction when the support member 20 supports the support location 30, and the lateral direction A can define the medial-lateral direction when the support member 20 supports the support location 30. Alternatively, the longitudinal direction L can define the medial-lateral direction when the support member 20 supports the support location 30, and the lateral direction A can define the cranial-caudal direction when the support member 20 supports the support location 30. Alternatively still, both the longitudinal direction L and the lateral direction A can be angularly offset with respect to each of the medial-lateral direction and the cranial-caudal direction.

In one example, the aperture 38 can be define any suitable shape as desired along a plane that is defined by the longitudinal direction L and the lateral direction A. In one example, the shape can be a substantially elliptical shape. Thus, a middle portion of the aperture 38 can have a width that is greater than a width of the aperture 38 that is outboard of the middle portion of the aperture 38 along the longitudinal direction L. In another example, the shape can be a substantially rectangular shape. The length of the aperture 38 along the longitudinal direction L can be within the range of approximately 2:1 to approximately 4:1 with respect to the width of the aperture 38 along the lateral direction A. In one example, the length of the aperture 38 along the longitudinal direction L can be approximately 3:1 with respect to the width of the aperture 38 along the lateral direction A. The ratio of the length to width can be selected to sufficiently reduce the amount of tension that the support member 20 places on the surgical wound 26 in the medial-lateral direction and cranial-caudal direction during operation of the support member 20. The interior surface 33 can likewise be spaced from the surgical wound 26 any distance as desired that is suitable to reduce the amount of tension that the support member 20 places on the surgical wound 26. Thus, a margin can be defined as a distance from the surgical wound 26 to the interior surface 33. The margin can be any distance as desired. In one example, the margin can be substantially equal to the thickness of the support member 20 along the transverse direction T when the support member is in the relaxed state. In one example, the margin can be at least one inch.

Figure 11:
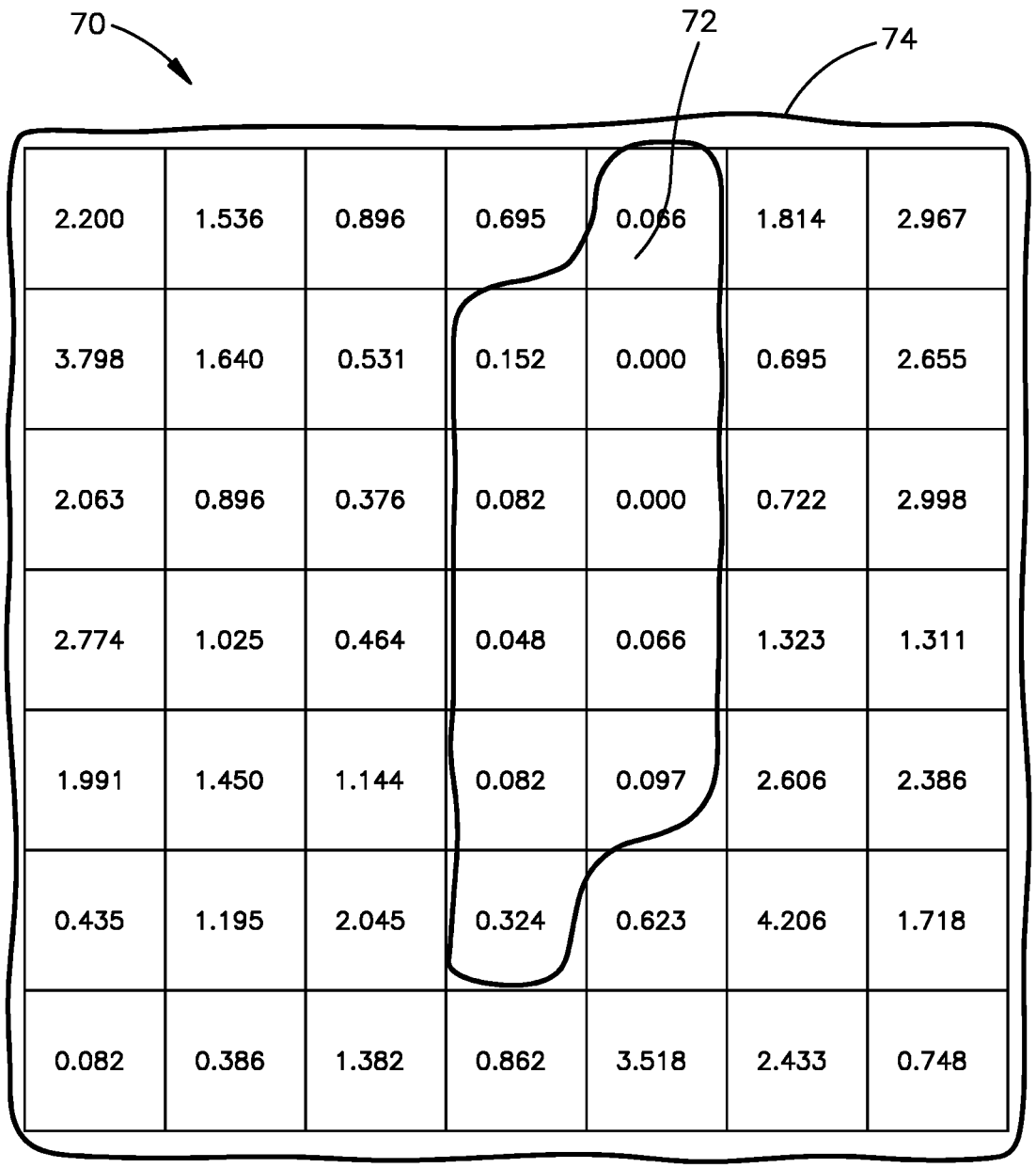
FIG. 11 is a plot that illustrates test data associated with a simulated use of the support member illustrated in FIG. 3.

Referring now to FIG. 11, the support member 20 was tested by placing the first surface 32 of the body 32 against a pressure pad, and subjecting the second surface 32b of the body 32 to 170 pounds of force. Thus, the pressure pad simulated the patient 24, and the applied force simulated the support surface 34. Pressure illustrated as pounds per square inch are illustrated on the plot 70 as measured by the pressure pad at different locations aligned with the body 32. An inner region of the pressure pad aligned with the aperture 38 along the transverse direction T is shown at an inner region 72 of the plot 70. An outer region of the pressure pad aligned with the first surface 32a of the body 32 along the transverse direction T is shown at an outer region 74 of the plot 70. The plot illustrates that the outer region of the pressure pad experienced forces that were greater than the forces experienced at the inner region of the pressure pad by an average ratio of approximately 16:1. This plot demonstrates the reduction of forces experienced by the patient 24 at the surgical site 27 when the surgical site 27 is aligned with the aperture 38 in the manner described above.

Figure 6A:
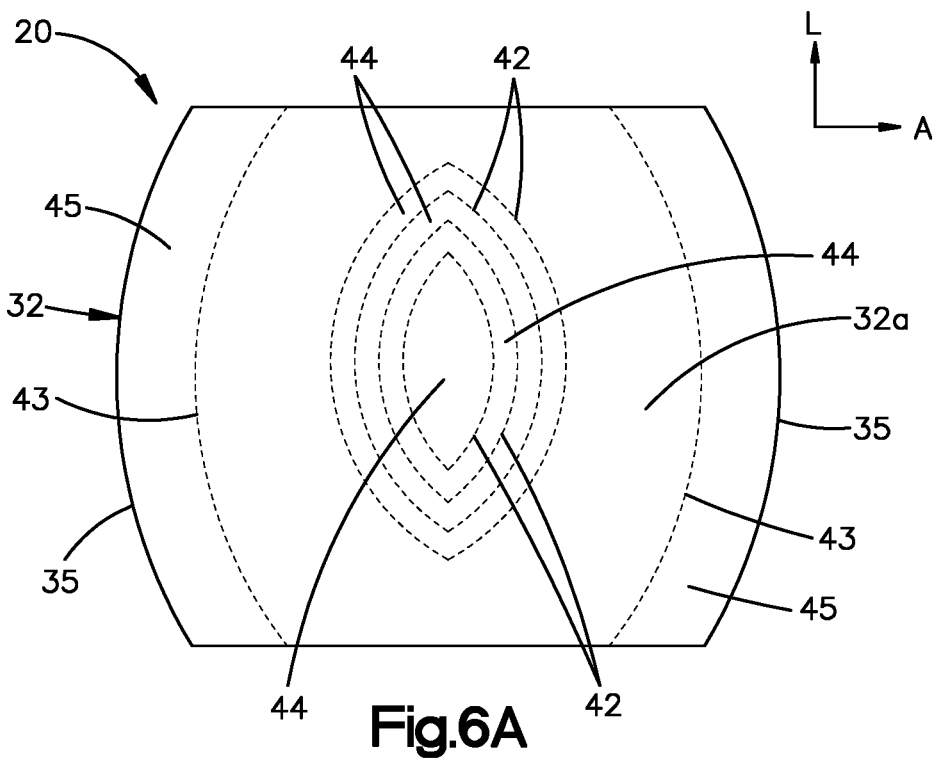
FIG. 6A is a top plan view of the support member as illustrated in FIG. 3, showing a plurality of perforations in accordance with one embodiment.

In one example, the support member 20 can be manufactured with the aperture 38 as described above. Referring to FIGS. 6A-B, in another example, the support member 20 can define at least one pre-defined aperture perforations 42, such as a plurality of aperture perforations 42. Each aperture perforation 42 can define a respective perforated region 44. The aperture perforations 42 can include an innermost aperture perforation and a plurality of outwardly spaced aperture perforations, each of the outwardly spaced aperture perforations surrounding respective inner ones of the aperture perforations 42. The aperture perforations can be evenly spaced or variably spaced from each other. Each aperture perforation 42 can substantially circumscribe the respective perforated region 44. As a result, the perforated regions 44 increase in size along an outward direction perpendicular to the transverse direction. The aperture perforations 42 can extend from the first surface 32a to the second surface 32b along the transverse direction T. Accordingly, a user can determine a desired size of the aperture 38, and remove a respective perforated region 44 so as to define the aperture 38 from the removed perforated region 44. Thus, the innermost perforated region 44 can define the inner surface 33. In another example, the support member 20 can be manufactured with the aperture 38 as described above, and can further include a plurality of aperture perforations 42 disposed outboard of the aperture 38. Thus, the perforated region 44 defined by selected one of the aperture perforations 44 can be removed so as to increase the size of the predefined aperture 38 to the desired size. FIG. 6B illustrates one of the perforated regions 44 removed from the body 32 at the respective aperture perforations 42 shown in FIG. 6A.

With continuing reference to FIGS. 6A-6B, the support member 20 can define a at least one plurality of pre-defined perimeter perforations 43. Each perimeter perforation 43 can define a respective at least one respective perforated region 45. The outermost perforated region 45 can define at least a portion of the outer perimeter 35. Each perforated region 45 can be removed so as to adjust one of the length and the width of the body 32. For instance, as illustrated, the support member 20 can include a pair of lateral perforated regions 45 that are spaced from each other along the lateral direction, and define the lateral boundaries of the outer perimeter 35. Thus, when one of the perforated regions 45 is removed, the width of the body 32 is reduced by the width of the perforated region 45 that was removed. FIG. 6B illustrates one of the perforated regions 45 removed from the body 32 at the respected perforations 43 shown in FIG. 6A.

Figure 7:
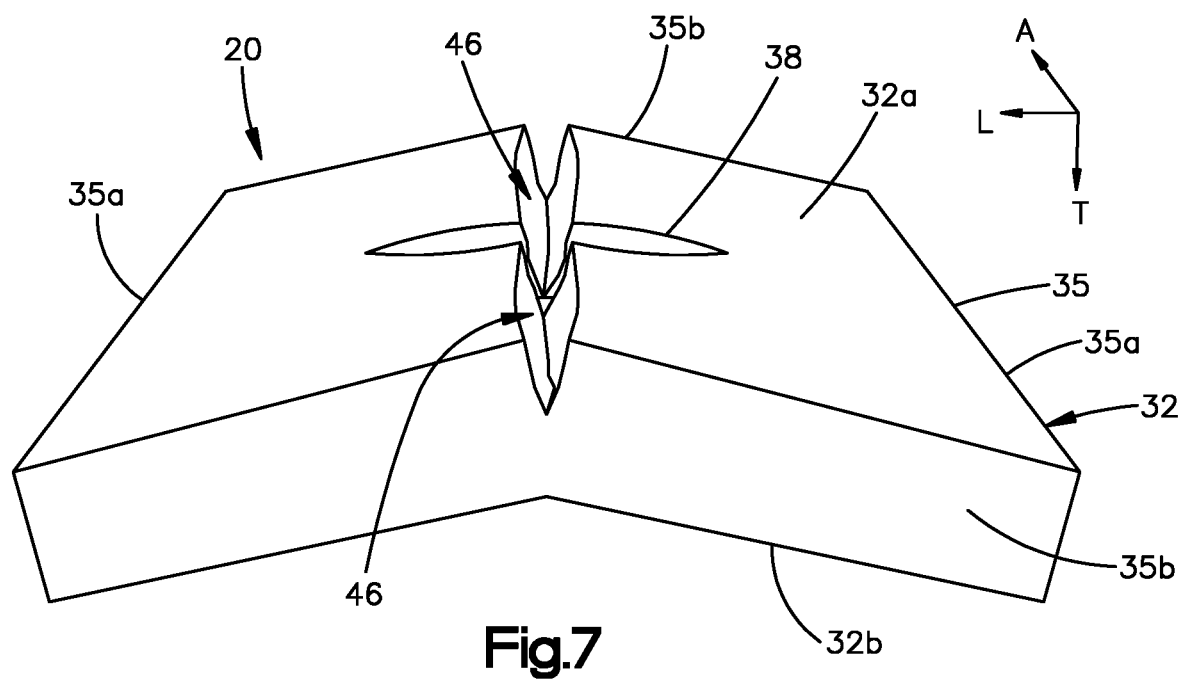
FIG. 7 is another perspective view of the support member illustrated in FIG. 4, showing a plurality of channels.

Referring now to FIG. 7, the support member 20 can define at least one channel 46, such as a plurality of channels 46 that are configured to place the surgical wound 26 in fluid communication with an environment that is external to the support member 20. The channels 46 can each extend from the outer perimeter 35 of the body 32 to the aperture 38. The channels 46 can be oriented along the lateral direction A, the longitudinal direction L, or any suitable direction that is angularly offset with respect to each of the lateral direction A and the longitudinal direction L. For instance, the outer perimeter 35 can include ends 35a that are opposed with respect to the longitudinal direction L, and sides 35b that are opposed with respect to the lateral direction A. The ends 35a and sides 35 can be adjoined at respective intersections. The channels 46 can extend from one or both of the ends 35a to the inner surface 33. Alternatively or additionally, the channels 46 can extend from one or both of the sides 35b to the inner surface 33. Alternatively or additionally, the channels 46 can extend from one or more of the interfaces to the inner surface 33 (see FIGS. 9-10). In one example, one or more up to all of the channels 46 can extend between the first and second surfaces 32a and 32b along the transverse direction T. For instance, the channels 46 can extend from one of the first and second surfaces 32a and 32b along the transverse direction T toward the other of the first and second surfaces 32a and 32b.

Figure 8A:
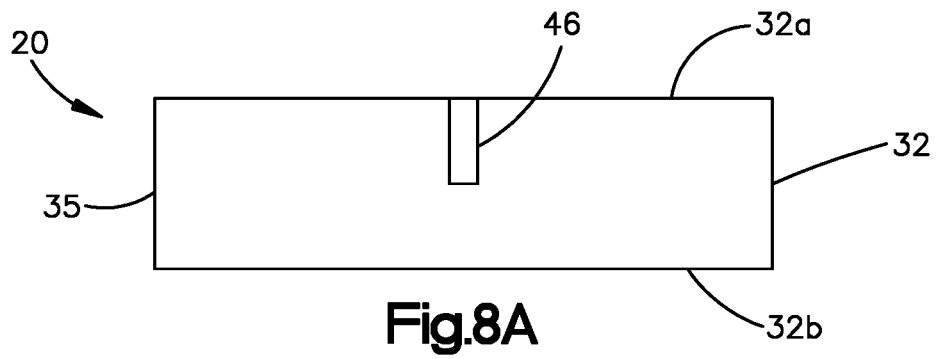
FIG. 8A is an elevation view of the support member as illustrated in FIG. 3, showing a channel constructed in accordance with one embodiment.

In one example illustrated in FIG. 8A, one or more of the channels 46 can terminate along the transverse direction T at a location between the first and second surfaces 32a and 32b.

Figure 8B:
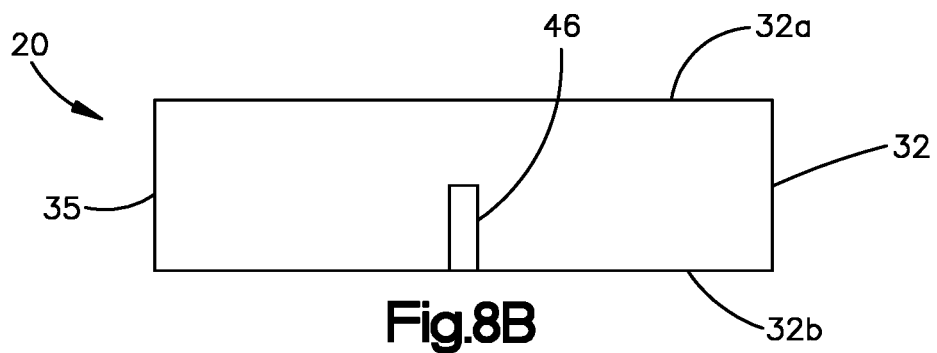
FIG. 8B is an elevation view of the support member as illustrated in FIG. 3, showing a channel constructed in accordance with another embodiment.
Figure 8C:
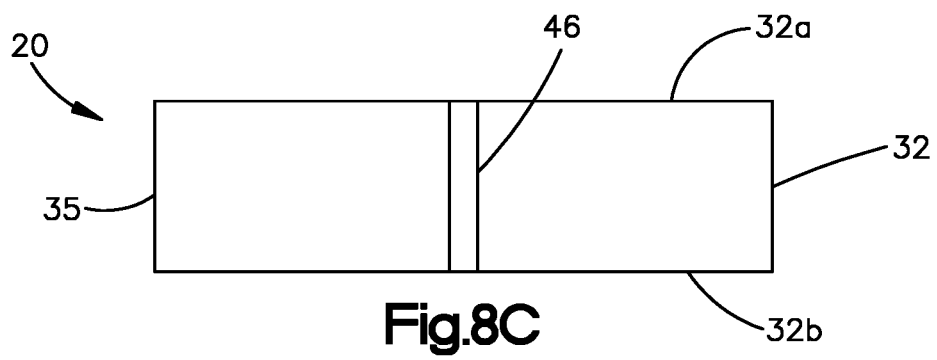
FIG. 8C is an elevation view of the support member as illustrated in FIG. 3, showing a channel constructed in accordance with another embodiment.
Figure 8D:
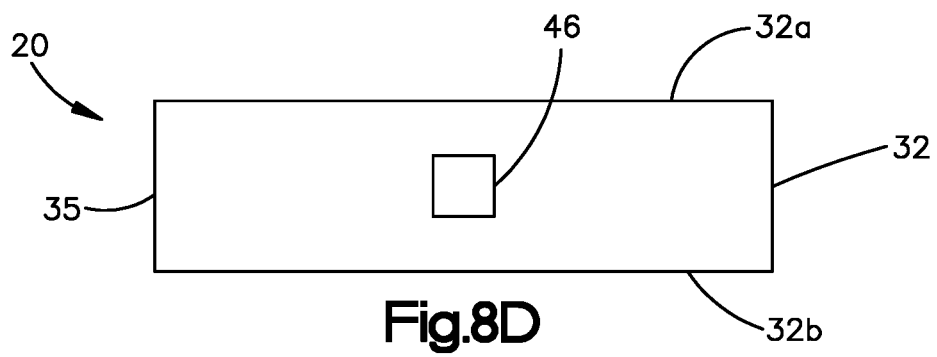
FIG. 8D is an elevation view of the support member as illustrated in FIG. 3, showing a channel constructed in accordance with another embodiment.

Thus, one or more of the channels 46 can extend from the first surface 32a toward the second surface 32b, and can terminate at a location between the first and second surfaces 32a and 32b. Alternatively or additionally, as illustrated in FIG. 8B, one or more of the channels 46 can extend from the second surface 32b toward the first surface 32a, and can terminate at a location between the first and second surfaces 32a and 32b. Alternatively or additionally, as illustrated in FIG. 8C, one or more of the channels 46 can extend from the first surface 32a to the second surface 32b. Alternatively still, as illustrated in FIG. 8D, an entirety of one or more of the channels 46 between the outer perimeter 35 and the aperture 38 can be disposed between the first and second surfaces 32a and 32b. Thus, the channel 35 is contained between the first and second surfaces 32a and 32b, and thus does not extend through either of the first and second surfaces 32a and 32b.

At least one or more up to all of the channels 46 can be configured to receive a respective conduit that is configured to extend from the aperture 38 through a respective one of the channels 46 to an environment that is external of the support member 20. For instance, the channels 46 can define a cross-sectional dimension suitable to receive a respective conduit. Alternatively, the compressibility of the material of the body 32 can cause the cross-sectional dimension of the channels 46 to expand and receive the respective conduit.

Figure 9:
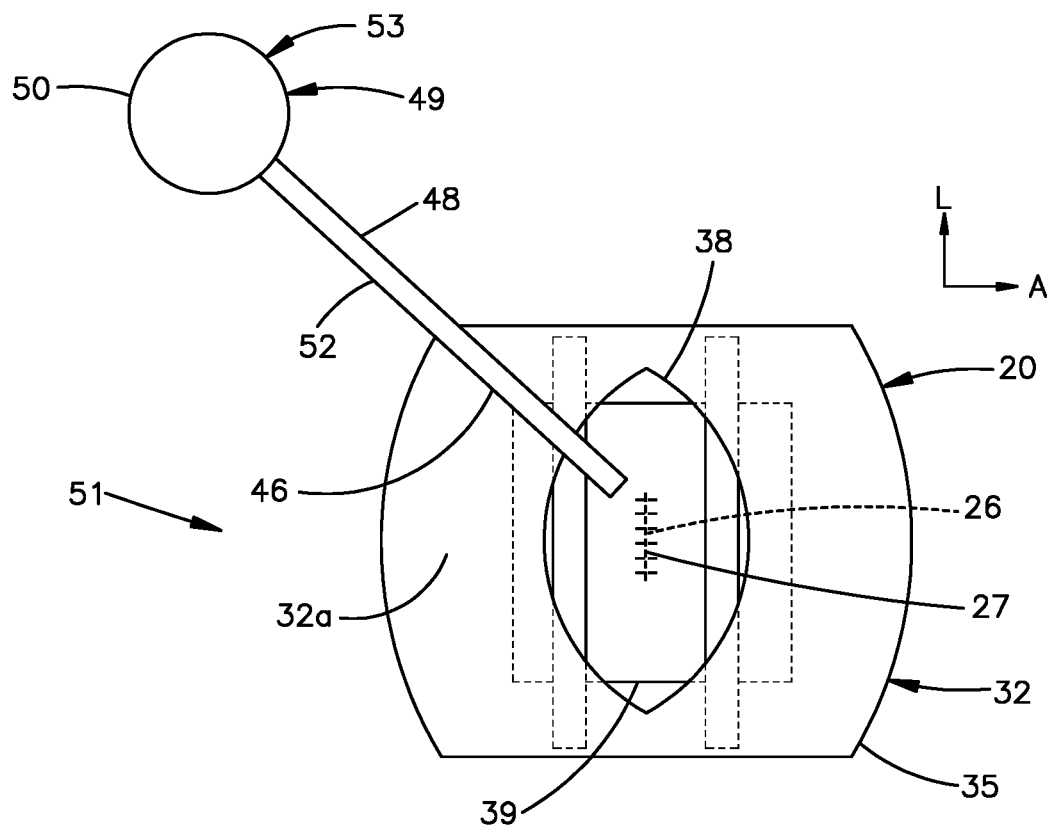
FIG. 9 is a schematic illustration of a wound treatment system that includes the spacer member and at least one wound drainage system.

Referring now to FIG. 9, in one example, a conduit 48 can be configured as a tube 52 of a wound drainage system 53 that is configured to remove serosanguinous fluid from the surgical site 27. For instance, a wound treatment system 51 can include at least one spacer member 20 and at least one wound drainage system 53. The wound drainage system 53 can, in one example, be configured as a Jackson-Pratt Drain (JP drain) 49. Thus, the wound treatment system can include at least one spacer member 20 and at least one JP drain 49, such as a plurality of JP drains 49. Each of the JP drains 49 can include a negative pressure inducement apparatus, such as a resiliently compressible bulb 50, and the tube 52 that extends from the bulb 50 through a respective one of the channels 46 to the surgical site 27. A first end of the tube 52 can be placed in fluid communication with the surgical wound 26, and a second end of the tube 52 opposite the first end can be placed in fluid communication with the interior of the bulb 52. For instance, the second end of the tube 50 can be attached to the bulb 52. The flexible bulb 50 can have a plug that can be opened to pour off collected fluid from the interior. To operate the JP drain, the bulb 50 is squeezed to evacuate air out of the interior of the bulb 50 so as to produce a vacuum in the interior that, in turn, creates suction in the tube 52. The suction causes the tube 52 to draw fluid from the surgical site 27 into the interior of the bulb 50. It should be appreciated that each of the channels 46 can be sized to receive one of the tubes 52 or a plurality of tubes 52. In one example, each of the channels 46 can be sized to receive a pair of the tubes 52.

Figure 10:
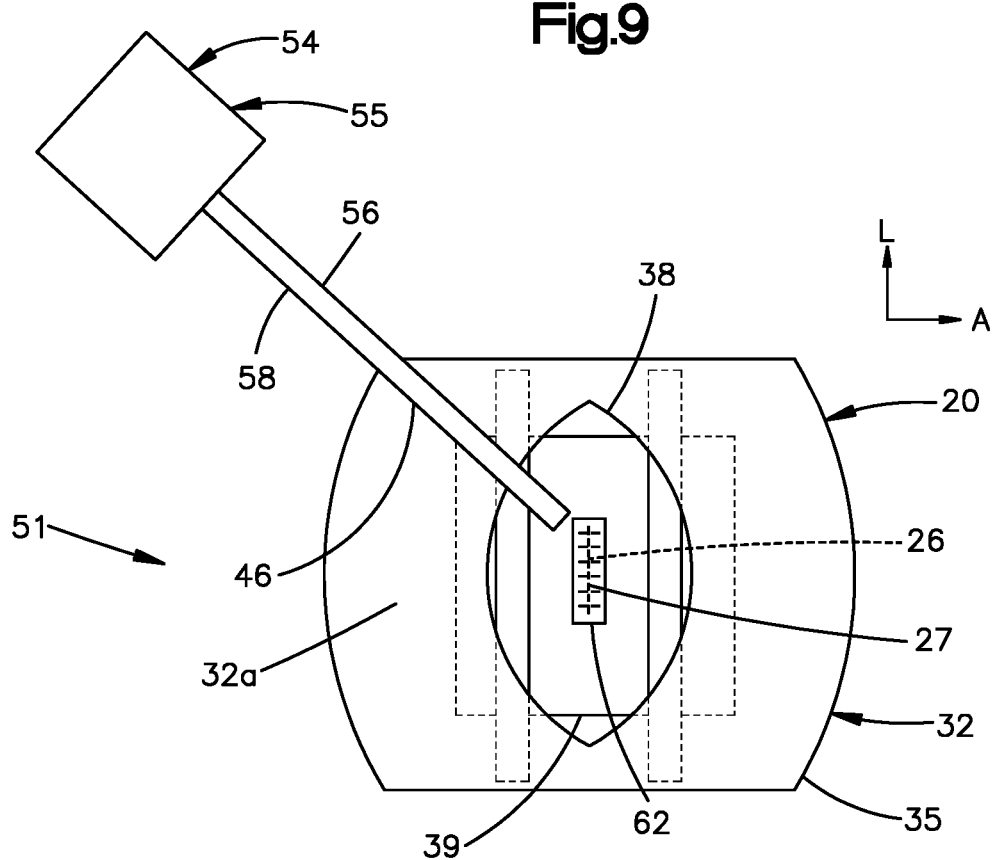
FIG. 10 is a schematic illustration of a wound treatment system that includes the spacer member and a negative pressure wound therapy apparatus.

Alternatively or additionally, as illustrated in FIG. 10, the wound treatment system 51 can include a negative pressure wound therapy apparatus 55 that is configured to produce negative pressure at the wound site 27 so as to promote healing of the surgical wound 26. In one example, the negative pressure wound therapy apparatus can be configured as a wound vacuum assisted closure (wound VAC) 54. The wound VAC 54, and thus the negative pressure wound therapy apparatus, can include a filler material 60 that is inserted into the surgical wound 26 and covered by an overlying cover 62. The wound VAC 54, and thus the negative pressure wound therapy apparatus, can further include a conduit 56 that can have a cross-sectional dimension greater than that of the conduit 46. The conduit 56 can be configured as a flexible tube 58 that, in turn, is configured to extend through the overlying cover so as to be placed in fluid communication with the surgical wound 26 at a first end. The wound VAC, and thus the negative pressure wound therapy apparatus, can further include a vacuum source that is configured to induce a negative pressure in the tube 58. In one example, the vacuum source can be configured as a pump, such as an electrical pump. The tube 58 can extend from the first end through a respective one of the channels 46, such that a second end of the tube 58 opposite the first end is placed in fluid communication with the pump. The negative pressure induced in the tube 58, turn, creates a negative pressure at the surgical wound 26, thereby promoting wound healing.

As described above, the wound treatment system can include a plurality of support members 20. For instance, the wound treatment system can include a kit of support members 20. Respective ones of the support members 20 of the kit can define at least one different characteristic than others of the support members 20 of the kit. For instance, the at least one different characteristic can be defined by at least one of the length of the aperture 38, the width of the aperture 38, the thickness of the aperture 38, the length of the support member 20, the width of the support member 20, the relaxed thickness of the support member 20, the material of the support member 20, the number of aperture perforations 42, the type of attachment member 36, and the porosity of the body 32. For instance, different ones of the bodies 32 of the kit can have porosities greater than or less than others of the bodies 32 of the kit. For instance, one of the support members 20 of the kit can have a length greater than at least one other of the support members 20 of the kit. In one example, the length of one of the support members 20 of the kit can be twelve inches long, while the length of another one of the support members 20 of the kit can be sixteen inches long. The kit can further include a plurality of support members 20 having the same characteristics, such that one of the support members 20 can replace a discarded support member.

It should be appreciated that a method is provided that isolates the anatomical forces of the supine patient 24 from the surgical wound with respect to the transverse direction T. The method can include the step of placing the support member between the patient 24 and the support surface 34 such that an entirety of the surgical wound 26 is aligned with the aperture 38. The method can further include the step of iterating the patient to a supine position against the support surface 34 such that the anatomical forces of the supine patient 24 are isolated from the support surface 34 with respect to the transverse direction T. The method can further include the step of attaching the first surface 32a to the surgical site 27. For instance, the method can include the step of adhesively attaching the first surface 32a to the surgical site 27. The method can further include the step of compressing the support member 20 between the supine patient 24 and the support surface 34 under the weight of the supine patient 24. The method can further include the step of conforming the first surface 32a to the supine patient 24.

The method can further include the step of operating one or both of the wound drainage system and the negative pressure wound therapy apparatus. For instance, one conduit can be placed in fluid communication with the wound site 27 at the first end, can extend through a respective one of the channels 46, and can be placed in fluid communication with the negative pressure inducement apparatus at the second end. Alternatively or additionally, one conduit can be placed in fluid communication with the wound site at the first end, can extend through a respective one of the channels 46, and can be placed in fluid communication with the vacuum source at the second end. For instance, the method can include the step of filling the surgical wound 26 with the filler material, covering the surgical wound 26 and the filler material with the cover, and placing the first end of the conduit through the cover in fluid communication with the surgical site 27, and thus the surgical wound 26.

The method can further include the step of removing the support member 34 from the patient 24. The method can then include the step of removing the post-surgical dressing 39 from the surgical site 27, and applying a new dressing over the surgical wound 26. Next, the method can include the step of repositioning the support member 20 between the patient 24 and the support surface 34 such that the surgical wound 26 is aligned with the aperture 38 along the transverse direction T. For instance, the attachment member 34 can be re-attached to the supine patient 24, for instance at the support location 30, as described above. Alternatively or additionally, at least one new attachment member 34 can be applied to the first surface 32a after the step of removing and before the step of repositioning, such that the method can include the step of attaching the new attachment member 34 to the support location 30. Alternatively, after the support member 20 is removed, a new support member can be positioned between the patient 24 and the support surface 34 such that the surgical wound 26 is aligned with the aperture 38 along the transverse direction T, as described above. For instance, the step of positioning the new support member further can include adhesively attaching the new support member 20 to the support location 30.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

What is claimed:

1. A wound treatment system comprising:
   a post-surgical support member configured to support a patient that is supine on a support surface following a surgical procedure that has created a surgical wound, the support member including:
   a compressible body having a first surface configured to face the supine patient, and a second surface opposite the first surface along a transverse direction and configured to face the support surface, wherein the first surface is substantially planar,
   wherein the support member defines an aperture that extends at least into the body from the first surface toward the second surface, the support member configured to be placed against the patient such that the surgical wound is in alignment with the aperture along the transverse direction so as to isolate an anatomical load between the surgical wound and the support surface along the transverse direction, the anatomical load produced by the weight of the supine patient; and
   at least one wound drainage system that includes a conduit that extends through the compressible body to the aperture, and a vacuum source that is coupled to the conduit so as to apply negative pressure to the surgical wound through the aperture.

2. The wound treatment system as recited in claim 1, wherein the aperture defines a length along a longitudinal direction that is perpendicular to the transverse direction, and a width along a lateral direction that is perpendicular to both the longitudinal direction and the transverse direction, wherein the length is greater than the width.

3. The wound treatment system as recited in claim 2, wherein the aperture is substantially elliptical along a plane that extends along the longitudinal direction and the lateral direction.

4. The wound treatment system as recited in claim 2, wherein the aperture is substantially rectangular along a plane that extends along the longitudinal direction and the lateral direction.

5. The wound treatment system as recited in claim 1, wherein the body includes an interior surface that defines a perimeter of the aperture, and the interior surface is configured to circumscribe the surgical wound when the first surface faces the supine patient and the second surface faces the support surface.

6. The wound treatment system as recited in claim 1, wherein the aperture extends through the body from the first surface to the second surface.

7. The wound treatment system as recited in claim 1, wherein the aperture terminates at a location between the first surface and the second surface.

8. The wound treatment system as recited in claim 1, wherein the body defines a plurality of aperture perforations that each defines a respective perforated region, wherein each of the perforated regions is removable so as to create the aperture.

9. The wound treatment system as recited in claim 8, wherein the plurality of aperture perforations includes an innermost aperture perforation and a plurality of aperture perforations that each surround respective inner ones of the aperture perforations.

10. The wound treatment system as recited in claim 1, further comprising an attachment member carried by the first surface, wherein the attachment member is removably attachable to a surgical site that includes at least one of the surgical wound and a surgical dressing that covers the surgical wound.

11. The wound treatment system as recited in claim 1, wherein the body is porous.

12. The wound treatment system as recited in claim 1, wherein the body is resiliently compressible along the transverse direction.

13. The wound treatment system as recited in claim 1, wherein the body comprises at least one of silicone and polyurethane.

14. The wound treatment system as recited in claim 1, wherein the body comprises a memory foam.

15. The wound treatment system as recited in claim 1, wherein the body defines at least one channel that extends from an outer perimeter of the body to the aperture, and the channel receives the conduit.

16. The sound treatment system as recited in claim 1, further comprising a negative pressure would therapy apparatus that comprises a filler material that is configured for insertion into the surgical would and a cover that is configured to cover the filler material.

17. The wound treatment system as recited in claim 1, comprising a relaxed thickness from the first surface to the second surface of between one-half inch and two inches.

18. The wound treatment system as recited in claim 1, wherein the first and second surfaces are substantially planar and oriented substantially parallel to each other.

19. A method of isolating anatomical forces of a supine patient from a sutured surgical wound, the method comprising the step of:

placing a post-surgical support member between the patient and a support surface following a surgical procedure that has created the surgical wound, wherein the placing step 1) causes a substantially planar first surface of a compressible body of the support member to face the supine patient, and 2) aligns an aperture of the support member with an entirety of the sutured surgical wound along a transverse direction, wherein the aperture extends at least into the compressible body from the first surface toward an opposed second surface of the compressible body; and iterating the patient to a supine position against the support surface such that the post-surgical support member supports the patient that is supine on the support surface, and the post-surgical support member isolates anatomical forces of the supine patient between the sutured surgical wound and the support surface with respect to the transverse direction, the anatomical forces produced by the weight of the supine patient, wherein when the patient is in the supine position, the second surface of the compressible body opposite the first surface along a transverse direction faces the support surface.

20. The method as recited in claim 19, further comprising the step of applying a negative pressure to the surgical wound through the aperture.

21. The method as recited in claim 19, further comprising the step of removing at least one of a plurality of perforated regions so as to enlarge the aperture.

* * * * *